(12) United States Patent
Blomgren et al.

(10) Patent No.: US 8,348,938 B2
(45) Date of Patent: Jan. 8, 2013

(54) APPARATUS, SYSTEMS AND METHODS FOR TREATING A HUMAN TISSUE CONDITION

(75) Inventors: Richard D. Blomgren, Dacula, GA (US); Dilip Paithankar, Natick, MA (US); Roelof Trip, Suwanee, GA (US); Roman Slizynski, Foothill Ranch, CA (US); Kathleen Beauchamp, Hoboken, NJ (US)

(73) Assignees: Old Dominian University Research Foundation, Norfolk, VA (US); Eastern Virginia Medical School, Norfolk, VA (US)

( * ) Notice: Subject to any disclaimer, the term of this patent is extended or adjusted under 35 U.S.C. 154(b) by 779 days.

(21) Appl. No.: 12/436,659

(22) Filed: May 6, 2009

(65) Prior Publication Data

US 2009/0281540 A1     Nov. 12, 2009

Related U.S. Application Data

(60) Provisional application No. 61/050,814, filed on May 6, 2008.

(51) Int. Cl.
A61B 18/18     (2006.01)
(52) U.S. Cl. .......................... 606/41; 606/34
(58) Field of Classification Search ............. 606/41, 606/40, 34; 604/20
See application file for complete search history.

(56) References Cited

U.S. PATENT DOCUMENTS

| | | |
|---|---|---|
| 1,645,215 A | 10/1927 | Bauer |
| 1,814,791 A | 7/1931 | Ende |
| 1,916,722 A | 7/1933 | Ende |
| 2,185,367 A | 1/1940 | Blumlein |
| 3,551,677 A | 12/1970 | Brewster |
| 3,571,746 A | 3/1971 | DeTemple et al. |
| 4,016,886 A | 4/1977 | Doss et al. |
| 4,667,161 A | 5/1987 | Wilcox |
| 4,878,793 A | 11/1989 | Hewison |
| 4,917,093 A | 4/1990 | Dufresne et al. |
| 4,955,378 A | 9/1990 | Grasso |
| 4,969,468 A | 11/1990 | Byers et al. |
| 5,019,034 A | 5/1991 | Weaver et al. |
| 5,085,639 A | 2/1992 | Ryan |
| 5,088,982 A | 2/1992 | Ryan |
| 5,118,969 A | 6/1992 | Ikezi et al. |
| 5,137,817 A | 8/1992 | Busta et al. |
| 5,138,270 A | 8/1992 | Nakata et al. |

(Continued)

FOREIGN PATENT DOCUMENTS

EP     1844750 A1     10/2007

(Continued)

OTHER PUBLICATIONS

International Preliminary Report, PCT/US2009/043024 dated Nov. 18, 2010.

(Continued)

*Primary Examiner* — Kevin C Sirmons
*Assistant Examiner* — Deanna K Hall
(74) *Attorney, Agent, or Firm* — Cook Alex Ltd.

(57) ABSTRACT

Apparatus, systems and methods for providing electrical energy to treat a tissue condition includes a high voltage pulse generator for generating short high voltage pulses of energy and a delivery device for receiving the pulses of energy. The delivery device includes at least a pair of needle electrodes for penetrating into the tissue and delivering the pulses of energy to the tissue.

10 Claims, 6 Drawing Sheets

U.S. PATENT DOCUMENTS

| | | |
|---|---|---|
| 5,211,660 A | 5/1993 | Grasso |
| 5,382,240 A | 1/1995 | Lam |
| 5,389,069 A | 2/1995 | Weaver |
| 5,458,597 A | 10/1995 | Edwards et al. |
| 5,464,386 A | 11/1995 | Hofmann |
| 5,527,352 A | 6/1996 | Vona |
| 5,536,267 A | 7/1996 | Edwards et al. |
| 5,593,429 A | 1/1997 | Ruff |
| 5,630,426 A | 5/1997 | Eggers et al. |
| 5,660,836 A | 8/1997 | Knowlton |
| 5,674,267 A | 10/1997 | Mir et al. |
| 5,688,233 A | 11/1997 | Hofmann et al. |
| 5,697,882 A | 12/1997 | Eggers |
| 5,702,359 A | 12/1997 | Hofmann et al. |
| 5,775,753 A | 7/1998 | Tetelboim |
| 5,778,894 A | 7/1998 | Dorogi et al. |
| 5,810,762 A | 9/1998 | Hofmann |
| 5,868,744 A | 2/1999 | Willmen |
| 5,871,469 A | 2/1999 | Eggers |
| 5,871,524 A | 2/1999 | Knowlton |
| 5,885,211 A | 3/1999 | Eppstein et al. |
| 5,911,223 A | 6/1999 | Weaver et al. |
| 5,928,159 A | 7/1999 | Eggers et al. |
| 5,947,964 A | 9/1999 | Eggers et al. |
| 5,954,717 A | 9/1999 | Behl et al. |
| 5,968,006 A | 10/1999 | Hofmann |
| 5,968,041 A | 10/1999 | Edwards |
| 5,993,434 A | 11/1999 | Dev et al. |
| 6,010,613 A | 1/2000 | Walters et al. |
| 6,014,584 A | 1/2000 | Hofmann et al. |
| 6,027,501 A | 2/2000 | Goble et al. |
| 6,043,066 A | 3/2000 | Mangano et al. |
| 6,050,992 A | 4/2000 | Nichols |
| 6,055,453 A | 4/2000 | Hofmann et al. |
| 6,068,650 A | 5/2000 | Hofmann et al. |
| 6,086,585 A | 7/2000 | Hovda et al. |
| 6,106,524 A | 8/2000 | Eggers et al. |
| 6,107,699 A | 8/2000 | Swanson |
| 6,117,660 A | 9/2000 | Walters et al. |
| 6,120,493 A | 9/2000 | Hofmann |
| 6,135,990 A | 10/2000 | Heller et al. |
| 6,135,998 A | 10/2000 | Palanker |
| 6,149,620 A | 11/2000 | Baker |
| 6,174,308 B1 | 1/2001 | Goble et al. |
| 6,176,857 B1 | 1/2001 | Ashley |
| 6,181,964 B1 | 1/2001 | Hofmann et al. |
| 6,190,381 B1 | 2/2001 | Olsen |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,224,592 B1 | 5/2001 | Eggers et al. |
| 6,228,078 B1 | 5/2001 | Eggers et al. |
| 6,264,652 B1 | 7/2001 | Eggers et al. |
| 6,296,638 B1 | 10/2001 | Davison et al. |
| 6,309,387 B1 | 10/2001 | Eggers et al. |
| 6,312,428 B1 | 11/2001 | Eggers et al. |
| 6,326,177 B1 | 12/2001 | Schoenbach et al. |
| 6,334,856 B1 | 1/2002 | Allen et al. |
| 6,346,103 B1 | 2/2002 | Korsec et al. |
| 6,350,262 B1 | 2/2002 | Ashley |
| 6,377,854 B1 | 4/2002 | Knowlton |
| 6,377,855 B1 | 4/2002 | Knowlton |
| 6,379,353 B1 | 4/2002 | Nichols |
| 6,381,497 B1 | 4/2002 | Knowlton |
| 6,381,498 B1 | 4/2002 | Knowlton |
| 6,387,380 B1 | 5/2002 | Knowlton |
| 6,402,742 B1 | 6/2002 | Blewett et al. |
| 6,405,090 B1 | 6/2002 | Knowlton |
| 6,413,255 B1 | 7/2002 | Stern |
| 6,413,256 B1 * | 7/2002 | Truckai et al. ............ 606/41 |
| 6,416,507 B1 | 7/2002 | Eggers et al. |
| 6,416,508 B1 | 7/2002 | Eggers et al. |
| 6,425,873 B1 | 7/2002 | Marchitto et al. |
| 6,425,912 B1 | 7/2002 | Knowlton |
| 6,430,446 B1 | 8/2002 | Knowlton |
| 6,443,914 B1 | 9/2002 | Costantino |
| 6,453,202 B1 | 9/2002 | Knowlton |
| 6,453,203 B1 | 9/2002 | Yamazaki |
| 6,461,350 B1 | 10/2002 | Underwood et al. |
| 6,461,354 B1 | 10/2002 | Olsen et al. |
| 6,461,378 B1 | 10/2002 | Knowlton |
| 6,470,216 B1 | 10/2002 | Knowlton |
| 6,475,191 B2 | 11/2002 | Tamura et al. |
| 6,482,201 B1 | 11/2002 | Olsen et al. |
| 6,491,669 B2 | 12/2002 | Ebara |
| D469,179 S | 1/2003 | Nakagami |
| 6,503,231 B1 | 1/2003 | Prausnitz et al. |
| 6,514,248 B1 | 2/2003 | Eggers et al. |
| 6,516,223 B2 | 2/2003 | Hofmann |
| 6,520,950 B1 | 2/2003 | Hofmann et al. |
| 6,567,694 B2 | 5/2003 | Hayakawa |
| 6,569,149 B2 | 5/2003 | Dev et al. |
| 6,569,159 B1 | 5/2003 | Edwards et al. |
| 6,572,613 B1 | 6/2003 | Ellman et al. |
| 6,582,237 B2 | 6/2003 | Jacobson |
| 6,589,786 B1 | 7/2003 | Mangano et al. |
| 6,603,998 B1 | 8/2003 | King et al. |
| 6,616,631 B2 | 9/2003 | Takagi |
| 6,632,193 B1 | 10/2003 | Davison et al. |
| 6,632,220 B1 | 10/2003 | Eggers et al. |
| 6,632,221 B1 | 10/2003 | Edwards et al. |
| 6,637,998 B2 | 10/2003 | Langan et al. |
| 6,638,254 B2 | 10/2003 | Nakagami |
| 6,641,580 B1 | 11/2003 | Edwards et al. |
| 6,656,167 B2 | 12/2003 | Numao |
| 6,673,072 B1 | 1/2004 | Garito et al. |
| 6,676,638 B2 | 1/2004 | Takagi |
| 6,697,670 B2 | 2/2004 | Chomenky et al. |
| 6,730,075 B2 | 5/2004 | Palanker |
| 6,733,485 B1 | 5/2004 | Whitehurst et al. |
| 6,743,211 B1 | 6/2004 | Prausnitz et al. |
| 6,760,627 B2 | 7/2004 | Carter et al. |
| 6,766,202 B2 | 7/2004 | Underwood et al. |
| 6,773,431 B2 | 8/2004 | Eggers et al. |
| 6,780,178 B2 | 8/2004 | Palanker |
| 6,782,283 B2 | 8/2004 | Schmidt et al. |
| 6,785,569 B2 | 8/2004 | Schmidt et al. |
| 6,786,891 B2 | 9/2004 | Hiejima |
| 6,795,728 B2 * | 9/2004 | Chornenky et al. ............ 607/2 |
| 6,821,274 B2 | 11/2004 | McHale et al. |
| 6,831,377 B2 | 12/2004 | Yampolsky et al. |
| 6,855,127 B2 | 2/2005 | Nakagami |
| 6,881,213 B2 | 4/2005 | Ryan et al. |
| 6,889,089 B2 | 5/2005 | Behl et al. |
| 6,892,099 B2 | 5/2005 | Jaafar et al. |
| 6,896,672 B1 | 5/2005 | Eggers et al. |
| 6,913,605 B2 | 7/2005 | Fletcher |
| 6,918,907 B2 | 7/2005 | Kelly et al. |
| 6,920,883 B2 | 7/2005 | Bessette et al. |
| 6,921,399 B2 | 7/2005 | Carmel et al. |
| 6,923,793 B2 | 8/2005 | Ishida |
| 6,949,096 B2 | 9/2005 | Davison |
| 6,961,603 B2 | 11/2005 | Merilainen |
| 6,974,453 B2 | 12/2005 | Woloszko et al. |
| 6,994,706 B2 | 2/2006 | Chornenky et al. |
| 7,004,942 B2 | 2/2006 | Laird et al. |
| 7,006,874 B2 | 2/2006 | Knowlton et al. |
| 7,010,356 B2 | 3/2006 | Jog et al. |
| 7,022,121 B2 | 4/2006 | Stern |
| 7,048,718 B1 | 5/2006 | Mithiue |
| 7,115,123 B2 | 10/2006 | Knowlton |
| 7,150,746 B2 | 12/2006 | DeCesare |
| 7,179,255 B2 | 2/2007 | Lettice et al. |
| 7,189,230 B2 | 3/2007 | Knowlton |
| 7,217,265 B2 | 5/2007 | Hennings et al. |
| 7,229,436 B2 | 6/2007 | Stern |
| 7,238,185 B2 | 7/2007 | Palanker |
| 7,270,658 B2 | 9/2007 | Woloszko et al. |
| 7,278,993 B2 | 10/2007 | Kelly |
| 7,357,802 B2 | 4/2008 | Palanker |
| 2001/0025176 A1 | 9/2001 | Ellsberry et al. |
| 2001/0049522 A1 | 12/2001 | Eggers et al. |
| 2002/0010491 A1 | 1/2002 | Schoenbach et al. |
| 2002/0034796 A1 | 3/2002 | Shastri et al. |
| 2002/0077627 A1 | 6/2002 | Johnson et al. |
| 2002/0087155 A1 | 7/2002 | Underwood et al. |

| | | |
|---|---|---|
| 2002/0120260 A1 | 8/2002 | Morris et al. |
| 2002/0120261 A1 | 8/2002 | Morris et al. |
| 2002/0128641 A1 | 9/2002 | Underwood et al. |
| 2002/0133137 A1 | 9/2002 | Hofmann |
| 2002/0133149 A1 | 9/2002 | Bessette |
| 2002/0146831 A1 | 10/2002 | Nolan et al. |
| 2002/0156471 A1 | 10/2002 | Stern et al. |
| 2002/0161418 A1 | 10/2002 | Wilkens et al. |
| 2002/0193784 A1 | 12/2002 | McHale et al. |
| 2002/0193831 A1 | 12/2002 | Smith, III |
| 2002/0198485 A1 | 12/2002 | Dev et al. |
| 2003/0009148 A1 | 1/2003 | Hayakawa |
| 2003/0009164 A1 | 1/2003 | Woloszko et al. |
| 2003/0045867 A1 | 3/2003 | Marchitto et al. |
| 2003/0069618 A1 | 4/2003 | Smith, III et al. |
| 2003/0083724 A1 | 5/2003 | Jog et al. |
| 2003/0088243 A1 | 5/2003 | Carmel et al. |
| 2003/0097129 A1 | 5/2003 | Davison et al. |
| 2003/0120269 A1 | 6/2003 | Bessette et al. |
| 2003/0149451 A1 | 8/2003 | Chomenky et al. |
| 2003/0153960 A1 | 8/2003 | Chornenky et al. |
| 2003/0170898 A1 | 9/2003 | Gundersen et al. |
| 2003/0199866 A1 | 10/2003 | Stern et al. |
| 2003/0212396 A1 | 11/2003 | Eggers et al. |
| 2004/0000316 A1 | 1/2004 | Knowlton et al. |
| 2004/0019371 A1 | 1/2004 | Jaafar et al. |
| 2004/0116986 A1 | 6/2004 | Cantoni et al. |
| 2004/0153057 A1 | 8/2004 | Davison |
| 2004/0158288 A1 | 8/2004 | Keisari et al. |
| 2004/0167458 A1 | 8/2004 | Draghia-Akli et al. |
| 2004/0181216 A1 | 9/2004 | Kelly et al. |
| 2004/0181217 A1 | 9/2004 | Edwards et al. |
| 2004/0186466 A1 | 9/2004 | Chornenky et al. |
| 2004/0193097 A1 | 9/2004 | Hofmann et al. |
| 2004/0204669 A1 | 10/2004 | Hofmann |
| 2004/0210214 A1 | 10/2004 | Knowlton |
| 2004/0229363 A1 | 11/2004 | Nolan et al. |
| 2004/0233944 A1 | 11/2004 | Dantus et al. |
| 2004/0249373 A1 | 12/2004 | Gronemyer et al. |
| 2005/0080409 A1 | 4/2005 | Young et al. |
| 2005/0131402 A1 | 6/2005 | Ciarrocca et al. |
| 2005/0171523 A1 | 8/2005 | Rubinsky et al. |
| 2005/0182462 A1 | 8/2005 | Chornenky et al. |
| 2005/0222565 A1 | 10/2005 | Manstein |
| 2005/0228373 A1 | 10/2005 | Kelly et al. |
| 2005/0234443 A1 | 10/2005 | Rioux et al. |
| 2005/0261672 A1 | 11/2005 | Deem et al. |
| 2005/0273092 A1 | 12/2005 | G. et al. |
| 2005/0282254 A1 | 12/2005 | Lulla et al. |
| 2006/0036210 A1 | 2/2006 | Zhang et al. |
| 2006/0036300 A1 | 2/2006 | Kreindel |
| 2006/0062074 A1 | 3/2006 | Gundersen et al. |
| 2006/0064083 A1 | 3/2006 | Khalaj et al. |
| 2006/0074313 A1 | 4/2006 | Slayton et al. |
| 2006/0161221 A1 | 7/2006 | Blackmore et al. |
| 2007/0010811 A1 | 1/2007 | Stern et al. |
| 2007/0060862 A1 | 3/2007 | Sun et al. |
| 2007/0060989 A1 | 3/2007 | Deem et al. |
| 2007/0088413 A1 | 4/2007 | Weber |
| 2007/0129759 A1 | 6/2007 | Colthurst |
| 2007/0142881 A1 | 6/2007 | Hennings |
| 2007/0239156 A1 | 10/2007 | Palanker |
| 2007/0239260 A1 | 10/2007 | Palanker |
| 2008/0027428 A1 | 1/2008 | Palanker |
| 2008/0039832 A1 | 2/2008 | Palanker |
| 2008/0103529 A1 | 5/2008 | Schoenbach et al. |
| 2008/0125774 A1 | 5/2008 | Palanker |
| 2008/0140066 A1 | 6/2008 | Davison |
| 2008/0188846 A1 | 8/2008 | Palanker |

FOREIGN PATENT DOCUMENTS

| | | |
|---|---|---|
| GB | 455492 | 10/1936 |
| WO | WO 99/62593 A1 | 12/1999 |
| WO | WO 03/075777 | 9/2003 |

OTHER PUBLICATIONS

International Search Report for PCT/US2009/043024 dated Jan. 22, 2010.

* cited by examiner

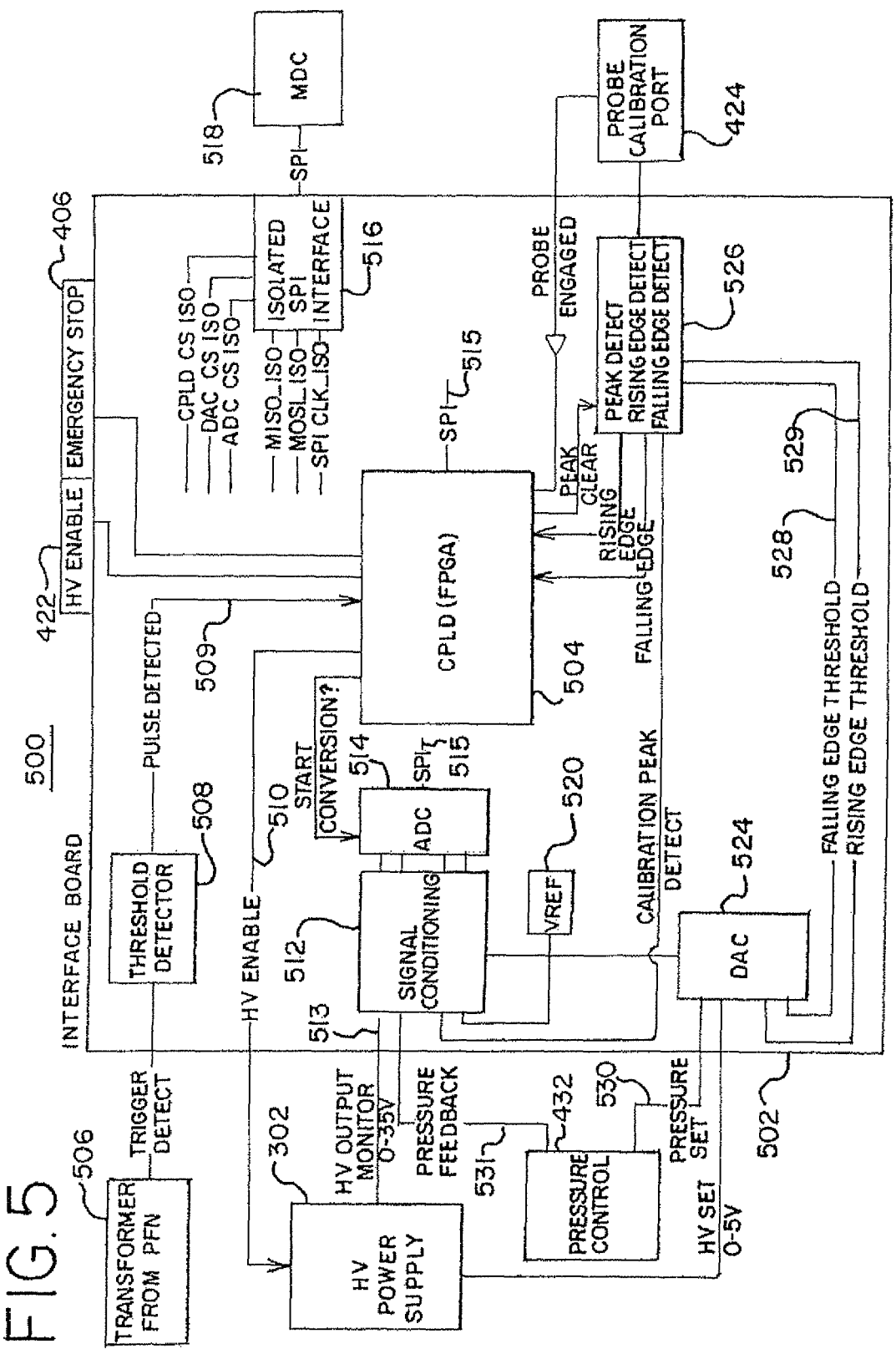

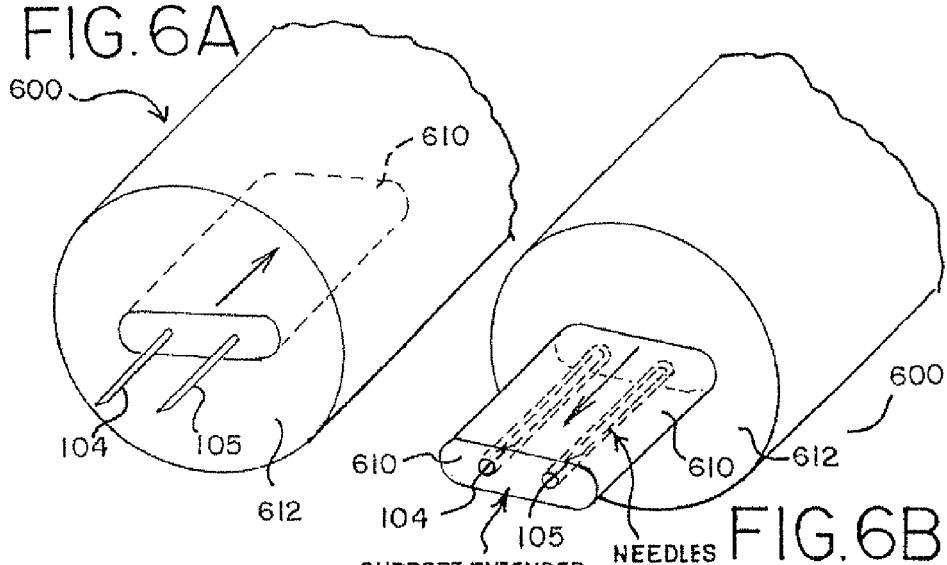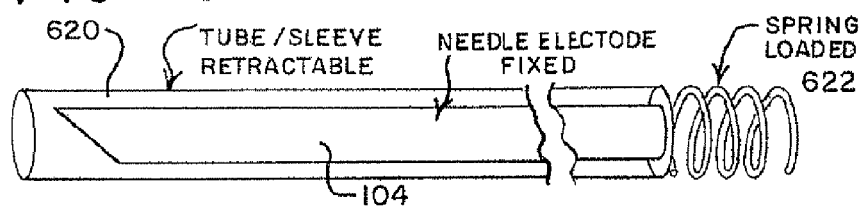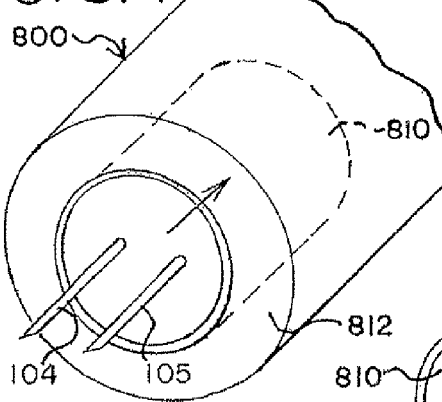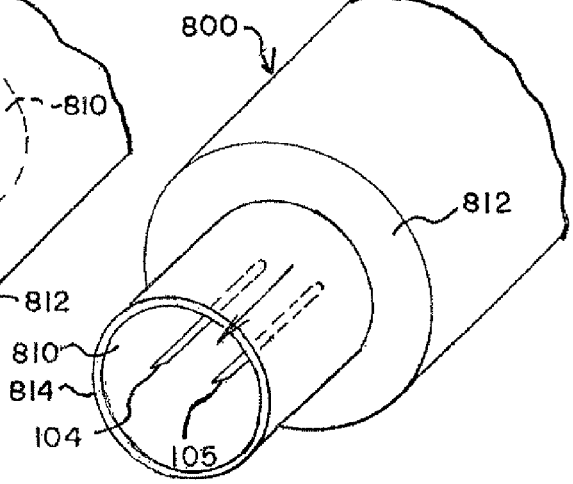

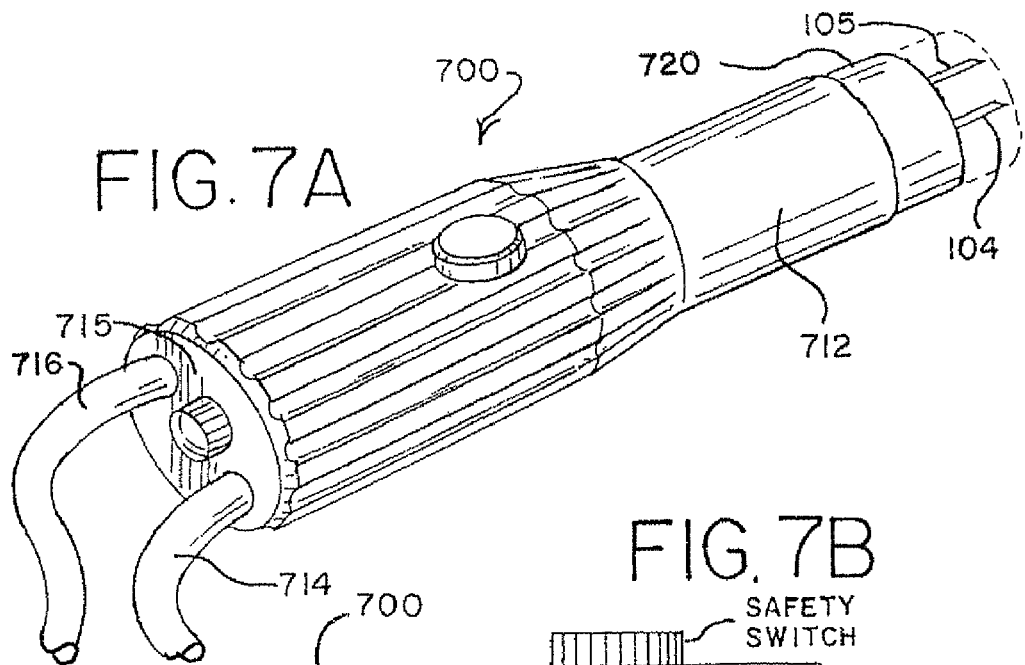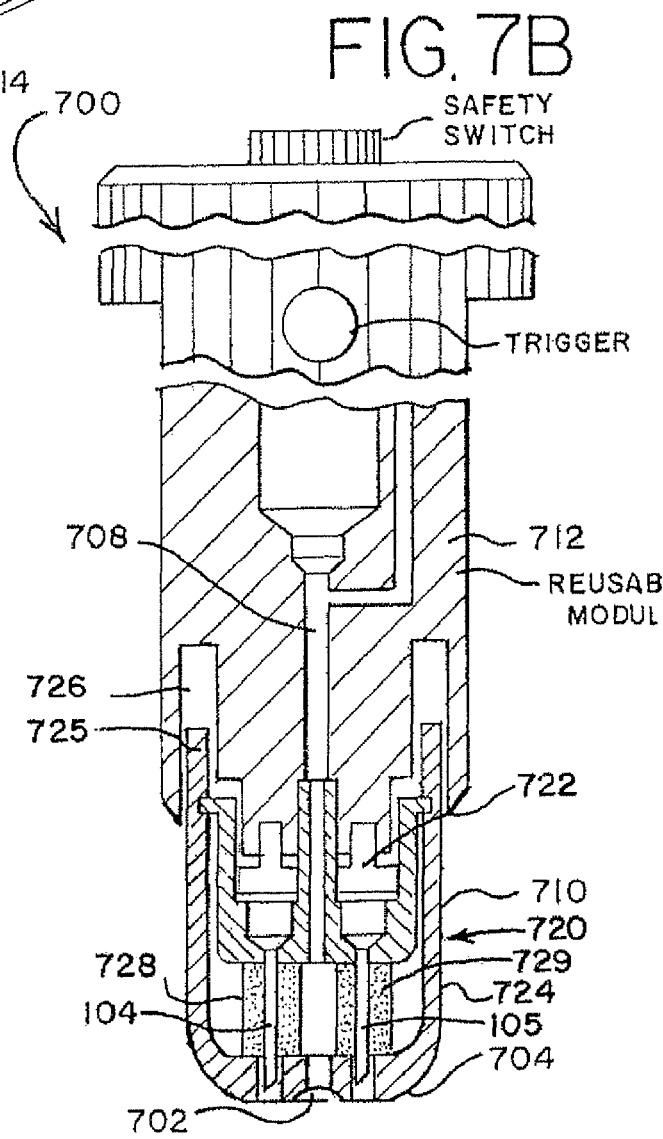

APPARATUS, SYSTEMS AND METHODS FOR TREATING A HUMAN TISSUE CONDITION

CROSS-REFERENCE TO RELATED APPLICATIONS

This patent application claims the benefit of, and the right of priority to, U.S. provisional patent application Ser. No. 61/050,814, filed on May 6, 2008.

FIELD

The present disclosure relates generally to apparatus and methods for providing electrical energy for tissue treatment.

BACKGROUND

U.S. Pat. No. 6,326,177 to Schoenbach et al., which is incorporated by reference herein in its entirety, describes an apparatus and method for intracellular electro-manipulation, including tissue treatment, using ultra short pulses. As taught by Schoenbach et al., target cells are subjected to one or more ultra short electric field pulses.

A general object of the subject matter disclosed herein is to therefore provide an improved delivery device for delivery of electrical energy for the treatment of a tissue condition.

Another general object of the subject matter disclosed herein is to provide an improved pulse generator for providing the electrical energy to the delivery device.

A further object of the subject matter disclosed herein is to provide a delivery device for delivery of electrical energy for the treatment of a tissue condition which is in the form of a dual or multiple needle assembly for penetration of the dermis.

Yet another object of the subject matter disclosed herein is to provide a dual or multiple needle assembly for the treatment of a tissue condition which is disposable.

A still further object of the subject matter disclosed herein is to provide insulation about portions of the dual or multiple needle assembly to protect the dermis during treatment of subcutaneous tissue.

Another object of the subject matter disclosed herein is to provide a pulse generator which generates low energy, high voltage pulses of short duration.

SUMMARY

The subject matter disclosed herein is directed to an apparatus, systems and methods for treating a tissue condition. In one embodiment, apparatus for providing electrical energy to human tissue to treat a tissue condition includes a high voltage pulse generator for generating a short high voltage pulse of energy at a pair of output terminals, a delivery device receives the short high voltage pulse of energy from the pulse generator, the delivery device preferably includes at least a pair of needle electrodes for penetrating into the human tissue and for delivering the short high voltage pulse of energy to tissue disposed between the needle electrodes.

The pair of needle electrodes of the delivery device preferably have uncoated ends, and have an insulative coating applied about proximal portions of the needle electrodes. The insulative coating may consist of parylene, polyimide, polyester, diamond, Teflon, or combinations of such materials, or another insulating material. When in use during a tissue treatment procedure, the uncoated portions of the needle electrodes are located in sub-dermal tissue and the coated portions of the needle electrodes are located in dermis. The short high voltage pulse may be in the range of about 10 to 500 nanoseconds in duration, and may provide average electric field strength of about 10 to 50 kilovolts/centimeter in the tissue. The tissue treatment procedure may include an intracellular electro-manipulation treatment or a plasma spark discharge.

In another embodiment, multiple needle electrodes will be used in an array. At any time, two selected electrodes will have the desired voltage applied across them. The selected electrodes may be selected with a switch, for example, based upon electromechanical relays.

In another embodiment, the subject matter disclosed herein is directed to a system for providing electrical energy to human tissue to treat a tissue condition. The system preferably includes a high voltage pulse generator for generating a short high voltage pulse of energy at a pair of output terminals, the pulse generator includes a spark gap which contains a pressurized gas and which emits a spark when the voltage across the spark gap exceeds the dielectric strength of the gas in the spark gap, a sensor for sensing the pressure of the pressurized gas in the spark gap and for providing a pressure signal related to the sensed pressure, means for adjusting the pressure in the spark gap to modify the magnitude of the voltage of the short high voltage pulse generated by the pulse generator, and a delivery device for receiving the short high voltage pulse of energy from the pulse generator and for applying the short high voltage pulse of energy to the tissue.

The means for adjusting the pressure in the spark gap may further include a controllable gas pressure regulator to supply gas pressure to the spark gap, means for selecting an initial voltage magnitude for the short high voltage pulse, means for determining the actual voltage magnitude of the short high voltage pulse and for providing a signal representative of the actual voltage magnitude of the short high voltage pulse, and a data processor for receiving the signal representative of the voltage magnitude of the short high voltage pulse, the data processor determining any difference between the selected voltage magnitude and the actual voltage magnitude of the short high voltage pulse, and the data processor supplying a corrective signal to the controllable gas pressure regulator to change the gas pressure in the spark gap to decrease the voltage magnitude of the short high voltage pulse if the actual voltage magnitude is greater than the selected voltage magnitude or to increase the voltage magnitude of the short high voltage pulse if the actual voltage magnitude is less than the selected voltage magnitude.

A triggered spark gap may also be employed. In this embodiment, the pressure in the spark gap switch is held high enough so that it does not trigger without an external stimulus. An external stimulus is provided when it is desired to turn on the spark gap switch, for example, at a preprogrammed interval and at the desired voltage after the operator presses the switch to impart the treatment.

The means for providing a signal representative of the actual voltage magnitude may be a resistor divider or a pulse transformer. The data processor may be selected from a group consisting of a field programmable gate array, a complex programmable logic device, a microprocessor or a microcontroller. The pulse generator may be a Blumlein pulse generator. The delivery device may have similar characteristics and properties as presented above.

The apparatus and system may further include a vacuum in the delivery device to assist in keeping a bottom face of the delivery device in contact with the human tissue during the treatment. A retractable needle support may protect the pair of needle electrodes from bending during insertion of the pair of needle electrodes into the human tissue. The ends of the pair of needle electrodes may be retracted into the delivery device and the ends of the pair of needle electrodes may be quickly forced into the human tissue upon actuation of the delivery device.

A further embodiment of the subject matter disclosed herein is directed to methods for providing electrical energy to human tissue to treat a tissue condition. The method includes the steps of generating a short high voltage pulse of energy at a pair of output terminals with a high voltage pulse generator, emitting a spark when the voltage across a spark gap associated with the pulse generator exceeds the dielectric strength of pressurized gas in the spark gap, sensing the pressure of the gas in the spark gap, providing a pressure signal related to the sensed pressure, adjusting the pressure in the spark gap to modify the magnitude of the voltage of the short high voltage pulse generated by the pulse generator, receiving the short high voltage pulse of energy from the pulse generator at a delivery device, and applying the short high voltage pulse of energy to the tissue.

The methods may include the further steps of supplying gas pressure to the spark gap from a controllable gas pressure regulator, selecting an initial voltage magnitude for the short high voltage pulse, determining the actual voltage magnitude of the short high voltage pulse, providing a signal representative of the actual voltage magnitude of the short high voltage pulse, receiving the signal representative of the voltage magnitude of the short high voltage pulse at a data processor, determining any difference between the selected voltage magnitude and the actual voltage magnitude of the short high voltage pulse and supplying a corrective signal to the controllable gas pressure regulator to change the gas pressure in the spark gap to decrease the voltage magnitude of the short high voltage pulse if the actual voltage magnitude is greater than the selected voltage magnitude or to increase the voltage magnitude of the short high voltage pulse if the actual voltage magnitude is less than the selected voltage magnitude.

The step of providing a signal representative of the actual voltage magnitude of the short high voltage pulse may be provided by a resistor divider or by a pulse transformer. Still further steps of the methods may include one or more of the steps of selecting the data processor from a group consisting of a field programmable gate array, a complex programmable logic device, a microprocessor or a microcontroller, disposing an impedance between the high voltage pulse generator and the delivery device to limit the current associated with the short high voltage pulse of energy when the tissue has high conductivity condition, providing a pair of needle electrodes in the delivery device for penetrating into the human tissue, delivering the short high voltage pulse of energy to tissue disposed between the needle electrodes, providing the needle electrodes with uncoated ends, and providing an insulative coating about proximal portions of the needle electrodes.

The methods may further include the step of providing a vacuum in the delivery device to assist in keeping a bottom face of the delivery device in contact with the human tissue during the treatment. Still further steps may include disposing a pair of needle electrodes in said delivery device for penetrating into the human tissue and for delivering the short high voltage pulse of energy to tissue disposed between the needle electrodes, retracting the ends of the pair of needle electrodes into the delivery device, and forcing the ends of the pair of needle electrodes into the human tissue upon actuation of the delivery device. Additional steps may include disposing a pair of needle electrodes in the delivery device for penetrating into the human tissue and for delivering the short high voltage pulse of energy to tissue disposed between the needle electrodes, providing a retractable needle support to protect the pair of needle electrodes from bending during insertion of the pair of needle electrodes into the human tissue, extending the retractable needle support about the ends of the pair of needle electrodes, and retracting said retractable needle support into the delivery device as the pair of needle electrodes are inserted into the human tissue.

BRIEF DESCRIPTION OF THE DRAWINGS

The subject matter disclosed herein, together with its objects and the advantages thereof, may best be understood by reference to the following description taken in conjunction with the accompanying drawings, in which like reference numerals identify like elements in the figures, and in which:

FIG. 5 is a block diagram of electronic circuitry for monitoring and controlling the pulse generator shown in FIG. 3;

FIGS. 6A and 6B are partial perspective views of an energy delivery device which utilize a needle support which may be extended to protect both needles when the delivery device is not in use;

FIG. 6C is an elevational view of a separate needle support, similar to the needle support in FIGS. 6A-6B, but with a retractable separate needle support provided for each needle;

FIG. 7A is an perspective view of another embodiment of the energy delivery device illustrated in FIG. 1;

FIG. 7B is a partial cross-sectional view of the energy delivery device shown in FIG. 7A, which illustrates another embodiment of a disposable needle assembly with the needle assembly providing protection of the dual needles when the energy delivery device is not in use;

FIGS. 8A and 8B are partial perspective views of an energy delivery device which are similar to FIGS. 6A-6B, but which provide a retractable cylindrical sleeve for protection of the needles when the delivery device is not in use.

DESCRIPTION OF THE PREFERRED EMBODIMENTS

It will be understood that the subject matter disclosed herein may be embodied in other specific forms without departing from the spirit thereof. The present examples and embodiments, therefore, are to be considered in all respects as illustrative and not restrictive, and the subject matter disclosed is not to be limited to the details presented herein.

The apparatus, systems and methods of the subject matter disclosed herein deliver pulsed electrical fields to sub dermal tissue of a human being. One such use is for the treatment of cellulite, by targeting fat cells and connective tissue. Other uses may include potential treatment of cancer, such as leukemia, may also be of interest.

Figure 1:
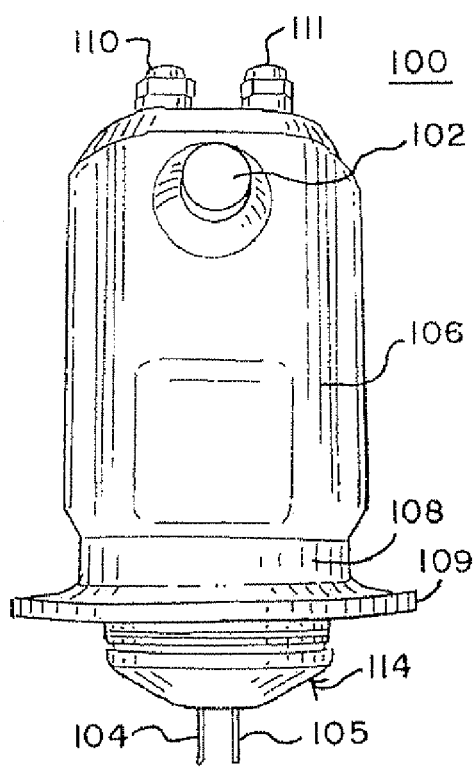
FIG. 1 is an elevational view of an energy delivery device in accordance with the subject matter disclosed herein.

One embodiment of an electrical pulse delivery device, generally designated 100, is shown in FIG. 1. Delivery device 100 provides ultra-short pulses of energy for an intracellular electro-manipulation or other treatment in accordance with the subject matter disclosed herein. A button 102 is disposed on the delivery device, such as near the top of delivery device 100. Button 102 operates as an electrical switch to provide electrical energy from a pulse generator 300 in FIG. 3 via a pair of input terminals 110-111 to a pair of needles 104 and 105 disposed on delivery device 100. For example, when button 102 is depressed, delivery device 100 provides pulses of energy from the pulse generator 300 to the pair of needles 104 and 105 for the intracellular electro-manipulation treatment. Upon release of button 102, the electrical path between the pulse generator 300 and the needles 104 and 105 is interrupted, and further treatment is automatically terminated.

Figure 2A:
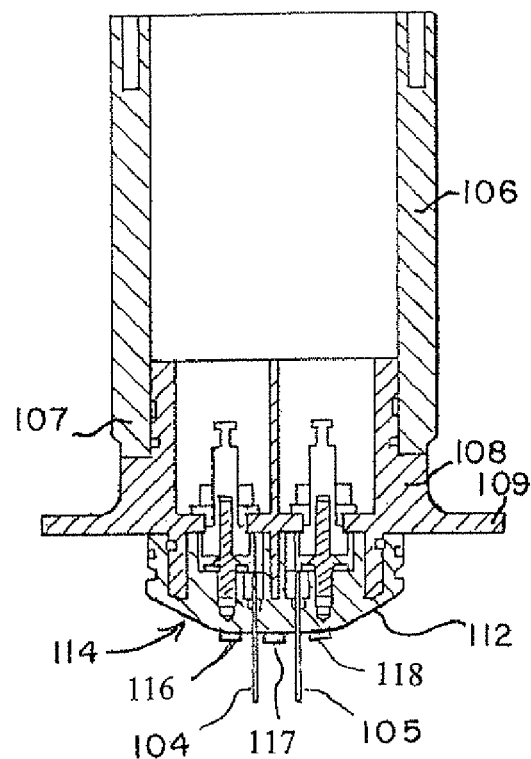
FIG. 2A is a partial longitudinal cross-sectional view of the energy delivery device of FIG. 1.

A portion of delivery device 100 includes a generally cylindrical housing 106. As seen in FIG. 2A, a lower end 107 of the housing 106 is suitable for receiving an adapter 108. Adapter 108 has a radially extending flange 109 of larger diameter than housing 106, which may assist a user in holding delivery device 100 during a treatment procedure. A dual needle assembly 114 (FIG. 2A) fits onto the bottom end of adapter 108. Dual needle assembly 114 may have an exterior domed surface 112 through which the pair of needles 104 and 105 extends downwardly.

Figure 2B:
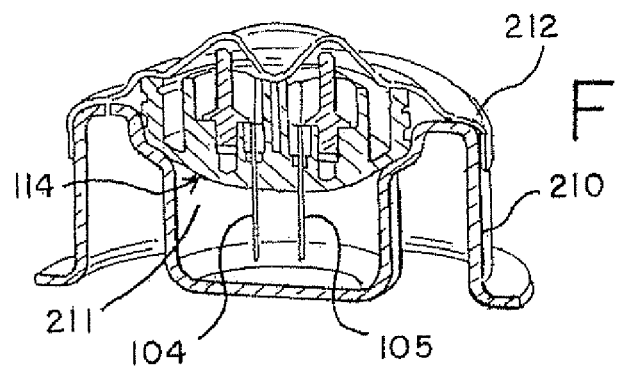
FIG. 2B is a cut-away perspective view of a dual needle adapter in sealed packaging for the energy delivery device of FIG. 1.

Preferably, the dual needle assembly 114 is disposable and is sealed for hygienic reasons. As shown in FIG. 2B, dual needle assembly 114 may come prepackaged. A lower package portion 210 provides a chamber 211 for protecting needles 104-105 prior to use, and an upper package portion 212 seals to lower package portion 210. Since needles 104 and 105 are intended to be electrically conductive to supply electrical energy to tissue to be treated, most of the remainder of assembly 114 is preferably constructed of an insulative material, such as an ABS (acrylonitrile butatiene styrene) plastic. Side portions of assembly 114 may provide a frictional fit to retain the assembly 114 onto the lower end of the adapter 108. Alternatively, assembly 114 may be threaded to secure assembly 114 to adapter 108.

Figure 2C:
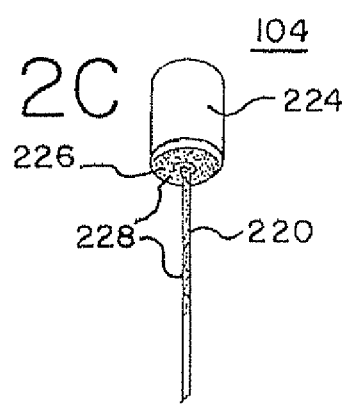
FIG. 2C is an enlarged perspective view of one of the needles in the dual needle adapter of FIG. 2B illustrating a coating which is applied to a portion thereof.

Needles 104 and 105 are preferably micro-needles, which may be made, for example, from solid 30 gauge stainless steel (316) stock. The tips of needles 104 and 105 may be hypodermic-style. That is, the tips may be formed with cutting edges to facilitate relatively painless and easy penetration of the skin. FIG. 2C illustrates one of the needles 104. As illustrated in FIG. 2C, a coating 228 is preferably applied to a proximal end 220 of needle 104, with the distal end 222 uncoated. An underside 226 of the head 224 of needle 104 may also have the coating 228 applied thereto.

The purpose of coating 228 at the upper end 220 of needle 104 is to avoid application of stronger electrical fields by delivery device 100 to dermal tissues while the lower uncoated end 222 is applying electrical fields to sub dermal tissue, such as fat cells and connective tissue called septae. Coating 228 is preferably relatively uniform in thickness and without any voids, such as pinholes. For example, coating 228 may be a parylene coating, which is deposited by a vapor-phase deposition polymerization process. Parylene has a low coefficient of friction, very low permeability to moisture and a high dielectric strength. Other examples for the coating 228 include polyimide, polyester, diamond, Teflon and siloxane. While needle 104 is shown in FIG. 2C and described above, it will be appreciated that needle 105 is similar to needle 104, including the coating 228. For hygienic reasons, the entire micro needle assembly 114, including needles 104 and 105, may be disposable.

For example, the needles 104 and 105 may extend about 5 mm to 15 mm, and, typically about 8 mm, from the bottom surface 112 of delivery device 100, with the proximal 3 mm to 5 mm of needles 104 and 105 having the insulating parylene coating 228. The parylene coating 228 is intended to extend through the dermis during a treatment procedure, thus protecting the dermis by substantially reducing the electrical field between needles 104 and 105 in the vicinity of the dermis. By way of example, the dual-needle delivery device 100 discussed herein may subject the target cells to a pulse in the range of 10 nanoseconds to 500 nanoseconds ($10 \times 10^{-9}$ seconds to $500 \times 10^{-9}$ seconds) having an average electric field strength ("E") of about 10 kV/cm to 50 kV/cm, and, typically of about 30 kV/cm, at a pulse rate of about 1 to 10 pulses per second.

With reference to FIG. 2A, the apparatus and system may also include one or more contact switches 116-118 at the distal face 114 of the delivery device 100 in contact with skin. A necessary condition for delivery of the electrical pulse can be activation of the contact switches when skin is pressed against the distal face 114, including one or any combination of the contact switches 116-118. This ensures that there is no significant air gap between the face 114 of the delivery device 100 and the skin, and consequently, the likelihood of energy delivery occurring on top of the skin surface is reduced or eliminated.

Figure 2D:
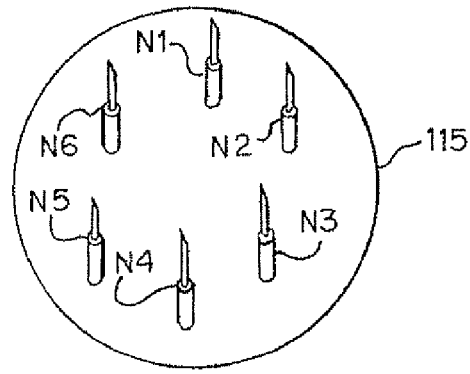
FIG. 2D is a plan view of an alternate needle assembly which has more than two needles for the energy delivery device of FIG. 1.

An alternate multiple needle array 115, which provides more than two needles 104-105 in the dual needle assembly 114, is shown in FIG. 2D. In the example of FIG. 2D, the multiple needle array 115 provides six needles N1 through N6. These needles may be partially insulated, as with needles 104-105. By way of example, voltage can be first applied between needles N1 and N2, then between needles N1 and N3, and so on. For N needles, the distinct number of pairs is (N*N−(N(N+1)/2))=36−21=15. These 15 pairs are N1-N2, N1-N3, N1-N4, N1-N5, N1-N6, N2-N3, N2-N4, N2-N5, N2-N6, N3-N4, N3-N5, N3-N6, N4-N5, N4-N6 and N5-N6. Voltage can be applied to all of these distinct pairs, or to some of these distinct pairs. Other configurations and choices of pairs are also contemplated.

Figure 3:
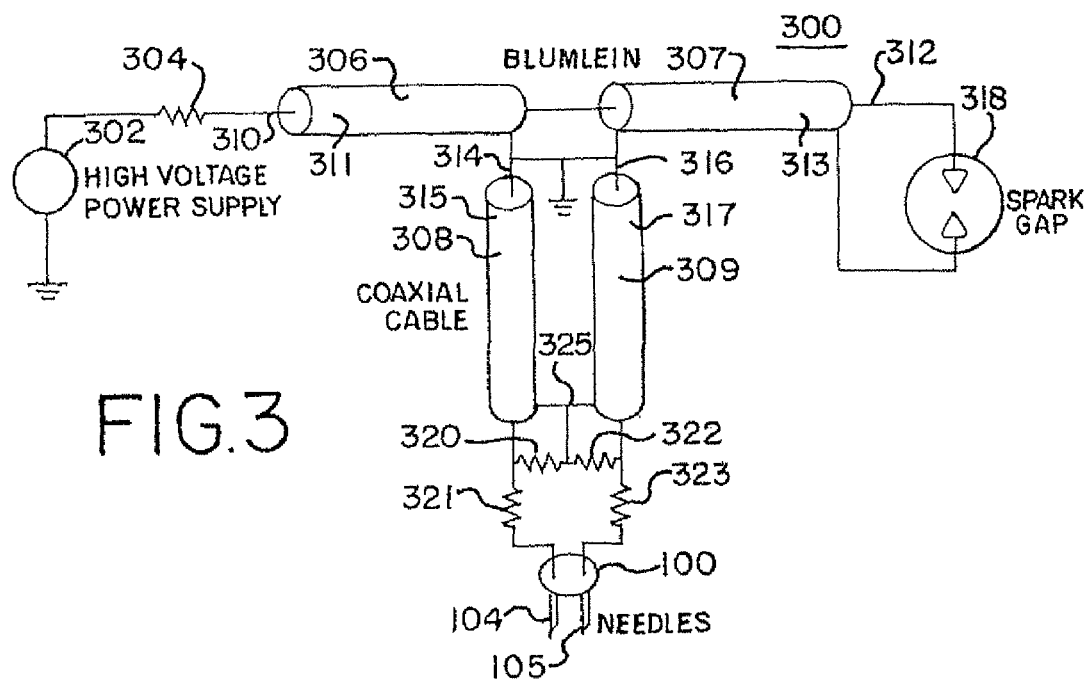
FIG. 3 is a diagram illustrating a Blumlein pulse generator for delivering high voltage pulses to the energy delivery device of FIG. 1.

As described above, the system delivers very short pulses of low energy to the tissue being treated. The schematic diagram in FIG. 3 illustrates a pulse generator, generally designated 300, of the Blumlein transmission line type, for generating low energy/high voltage pulses of short duration. In this embodiment, the ultra-short pulses are generated by pulse generator 300, but such pulses could also be generated using a pulse-forming network or by any other suitable methods. Pulse generator 300 generally consists of a high voltage power supply 302, four sections of coaxial cable 306-309 and a spark gap 318. A resistor 304 may be disposed between the high voltage power supply and the first coaxial section 306.

Inner conductors 310 and 312 of coaxial sections 306 and 307 connect to one of the leads of the spark gap 318. The other lead of spark gap 318 connects to the outer sheath 313 of coaxial section 307. Near coaxial sections 308 and 309, the outer sheaths 311 and 313 of coaxial sections 306 and 307 are grounded, as well as the inner conductors 314 and 316 of coaxial sections 308 and 309. At the opposite ends of coaxial sections 308 and 309, the outer sheaths 315 and 317 are connected together at a node 325. Inner conductor 314 of coaxial section 308 is connected to a pair of resistors 320 and 321, and inner conductor 316 of coaxial section 309 is similarly connected to another pair of resistors 322 and 323. Opposite ends of resistors 320 and 322 are connected to node 325. Opposite ends of resistors 321 and 323 are connected to needles 104 and 105, respectively. Collectively, resistors 320-323 form a balanced resistor network at the output of pulse generator 300.

The spark gap 318 may be filled with nitrogen or any other suitable gas. The internal pressure of the nitrogen in the spark gap may be regulated to control the voltage at which the spark gap breaks down, thereby also controlling the amount of energy delivered to the needles 104 and 105 by the pulse generator 300. When the spark gap breaks down, a high voltage, short duration pulse will be delivered to the needles through the balanced resistor network consisting of resistors 320-323. In an embodiment, all of resistors 320-323 may be about 50 ohms. The magnitude of the voltage delivered to the patient is determined by the spark gap 318. The spark gap will breakdown when the voltage across its electrodes exceeds the dielectric strength of the gas in the spark gap. The dielectric strength of the gas is controlled by the gaseous pressure within the spark gap. Thus, controlling the gaseous pressure also controls the magnitude of the voltage delivered.

In order to safely and reliably deliver short high-voltage pulses to a patient during a treatment procedure, adequate controls and monitors are required. The subject matter disclosed herein is also concerned with such controls and monitors. The first set of controls relate to ensuring that the voltage delivered to the patient is correct and accurate. The voltage delivered to the patient is selected by the operator through a user interface module, generally designated 400 in FIG. 4. Module 400 may include a power entry module with a power switch 402, indicators 404 for power on and alerts, such as light emitting diodes (LEDs), an emergency stop switch 406 and a touch sensitive screen 408 for displaying and selecting operating modes, menus of available options, and the like.

Associated with user interface module 400 is a high voltage control module 420. Module 420 may include a high voltage enable switch 422, a probe (also referred to herein as delivery device 100) calibration connection 424, a high voltage output 426 for supplying the high voltage pulses to delivery device 100, and a low voltage connection 428 for the delivery device 100. A regulator 432 monitors and supplies nitrogen gas to spark gap 318 from a source of compressed nitrogen 430.

Figure 4:
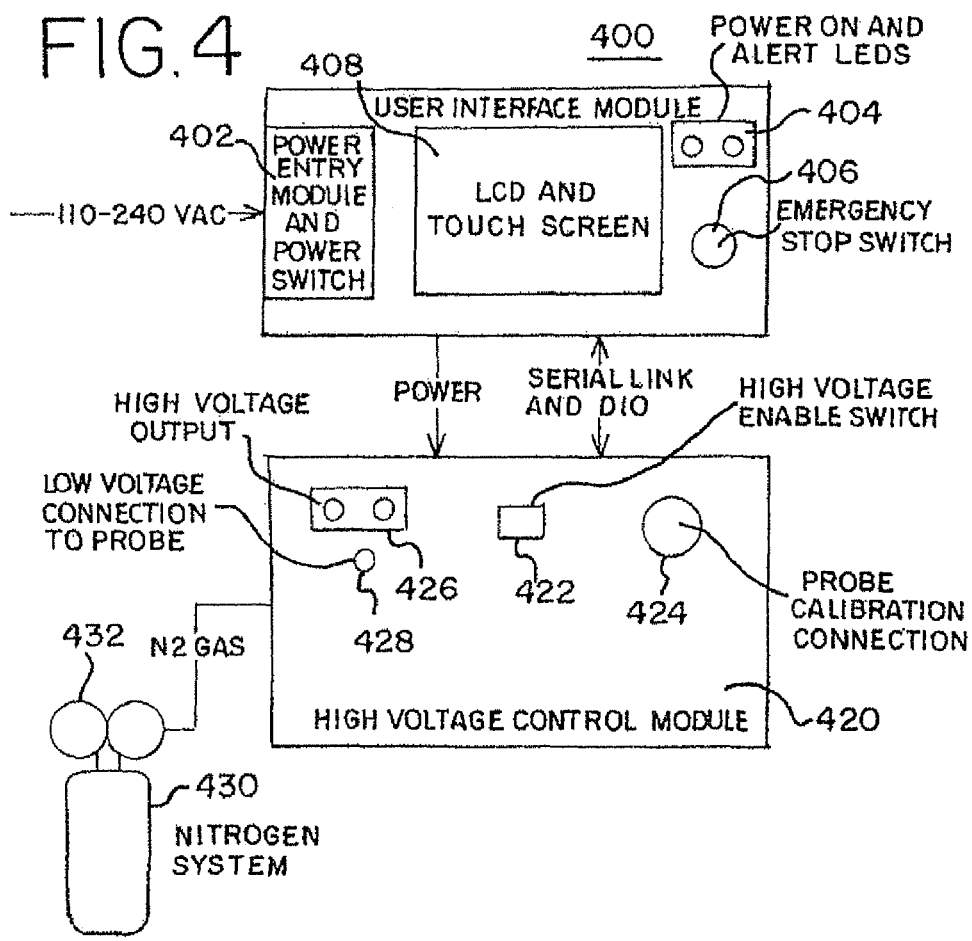
FIG. 4 is a diagrammatic view of a user interface for controlling the pulse generator shown in FIG. 3 in accordance with a further aspect of the subject matter disclosed herein.

FIG. 5 illustrates, in block diagram format, the electronic circuitry, generally designated 500, which may be contained within the high voltage control module 420 shown in FIG. 4. Much of circuitry 500 may be on a interface circuit board 502. Circuitry 500 is monitored and controlled by a complex programmable logic device (CPLD) 504. Alternatively, CPLD 500 may be a field-programmable gate array (FPGA) or any suitable microprocessor or microcontroller. The high voltage (HV) pulses generated by pulse generator 300 and supplied to delivery device 100 may be monitored in any of a variety of ways. For example, the HV pulses may be monitored by sensing the voltage across one of the resistors 321 or 323 in FIG. 3. A resistor divider (not shown) may be connected across resistor 321 to reduce the high voltage pulse to a lower level more suitable for the electronic circuitry 500. A pulse transformer 506 may be used to supply the pulse to circuitry 500, while also providing DC isolation between the circuitry and the pulse generator. A threshold detector 508 receives pulse signals from transformer 506 and provides pulse detection information to CPLD 504 via line 509 if any pulse exceeds a predetermined threshold.

CPLD 504 enables the HV power supply 302 via line 510. Signal conditioning circuitry 512 monitors the output voltage of the HV power supply on line 513. In this respect, signal conditioning circuitry 512 may have a voltage reference for comparison purposes. An analog to digital converter (ADC) 514 supplies the monitored information to CPLD 504 via a serial peripheral interface (SPI) bus. The SPI bus is also routed to other portions of the circuitry 500, such as to an isolated SPI interface 516 which may supply information to external sources, such as a master data controller 518.

Digital information concerning falling edge threshold and rising edge threshold is provided from peak detector 526, via lines 528 and 529, to a digital to analog converter (DAC) 524. DAC 524 then provides a pressure set signal on line 530 to pressure control 432 to regulate the pressure of nitrogen in the spark gap 318. As previously explained, control of the pressure in spark gap 318 controls the magnitude of the high voltage pulses generated by pulse generator 300. Pressure feedback information is provided from pressure control 432 on line 531 to the signal conditioning and thence to ADC where it is sent via the SPI bus to CPLD 504.

The CPLD or microprocessor 504 controls the gas pressure regulator 432 in setting and monitoring the gaseous pressure within the spark gap 318. The microprocessor also monitors the voltages going to the Blumlein pulse generator 300 and the voltage across the load resistors 320-323 on the output of the pulse generator using resistor dividers, pulse transformer 506 and analog to digital converter 514. Prior to use on the patient, the delivered voltage at the needles 104-105 is adjusted to ensure a proper value. This process starts by setting the spark gap pressure to an empirically generated first guess estimated to give the proper voltage. The Blumlein pulse generator 300 is fired and the pulse generator voltages are monitored. The pressure is then adjusted based on the difference between the measured output voltage and the desired output voltage. The adjustment process continues until the difference between the measured and desired is within an acceptable level.

The adjustment is preferably proportional control. However, the adjustment could also include differential and integral control. The control can be based on either the monitored pulse generator input or output signal. Using the pulse generator input signal requires monitoring the input voltage and holding the peak value from the time that the high voltage power supply (HVPS) 302 is activated until the pulse is delivered at the needles 104-105. Delivery of the pulse can be detected by either sensing a rapid decrease in the pulse generator input, a pulse on the pulse generator output or an optical signal from the spark gap. Using the pulse generator output signal may require detecting the rising and falling edges of the pulse and averaging the values between these two edges.

An alternate method for monitoring the voltage is to implement a calibration port 424 on the system. This calibration port 424 allows the distal end of the delivery device 100 to be connected to the console 420. The distal electrode voltage is then monitored and the spark gap pressure is controlled to ensure that the distal electrode voltage matches the desired output voltage within appropriate limits. This method will compensate for any losses or changes to the voltage induced by the patient cable and/or the delivery device.

A second set of controls is related to controlling the pulse delivery rate. The control of the pulse delivery rate is selected by the operator through the user interface 400. The microprocessor 504 controls the delivery of each pulse by commanding the HVPS 302 to go to a predetermined high voltage level that is selected to be higher than the desired voltage delivered to the patient. In this embodiment, the microprocessor controls the HVPS command through a field programmable gate array (FPGA) 504. This FPGA buffers the command to the HVPS 302 and controls the slope of the command to mitigate against excessive overshoot of the HVPS output. The output of the HVPS is feed into the pulse generator 300 through a series resistor and appropriate protection diodes. The microprocessor 504 will initiate these pulses at the rate determined by the user interface 400, such as by selection on screen 408. Several monitors ensure that the pulses delivered are within predetermined parameters. If any of these monitors indicate that the pulse has not been delivered, microprocessor 504 will inhibit any new pulses from being initiated and will alert the operator to the problem.

One risk for any high voltage delivery system is that some other component in the system breaks down at a lower voltage than the spark gap 318. If this occurs, no pulse, an improperly shaped pulse or a lower voltage pulse could be delivered to the patient. If any failures within the system are detected or if delivered pulses are not within established parameters, subsequent delivery of pulses will be terminated and the operator will be alerted.

In accordance with another aspect, the subject matter disclosed herein may be used by a physician to treat cellulite by inducing selective adipocyte death in the subcutaneous fat layer (SFL), or cutting of collageneous septae, or both, such as by plasma spark discharge. Adipocyte death may be caused by apoptosis or necrosis, both considered cell lysis. The dead adipocytes will be naturally reabsorbed by the body. Fewer adipocytes in the SFL will reduce the pressure on the dermis, blood vessels and lymphatic system in the affected area, which will typically lead to an improved cosmetic experience. The subject matter disclosed herein may also have an effect of cutting or ablating or denaturing septae that tether the dermis to the underlying fascia. These effects on the septae will lead to improvement in the appearance of cellulite dimples, for example, by releasing the tension on the dermis.

In accordance with a further aspect of the subject matter disclosed herein, needles 104-105 may be force assisted for insertion into the skin. One of the problems associated with small gauge needles, such as about 30 gauge needles, is that they tend to bend while insertion into the skin if the needles are not substantially perpendicular to the skin during insertion. Thus, care must be taken while inserting the needles into the skin to apply forces perpendicular to the skin surface, and in the direction of the needles, to avoid bending the needles. Thus, in accordance with another aspect of the subject matter disclosed herein, the needles 104-105 may be retractable into the delivery device 100. Upon actuation, the needles 104-105 are quickly forced or shot out to their full distal position, as illustrated in FIG. 1. The needles 104-105 are then held in this distal position by mechanical means or by application of force from the power source while therapeutic electrical pulses are delivered through the needles to the patient. Following the electrical pulse treatment, the needles may again be retracted into the delivery device 100.

Figure 9:
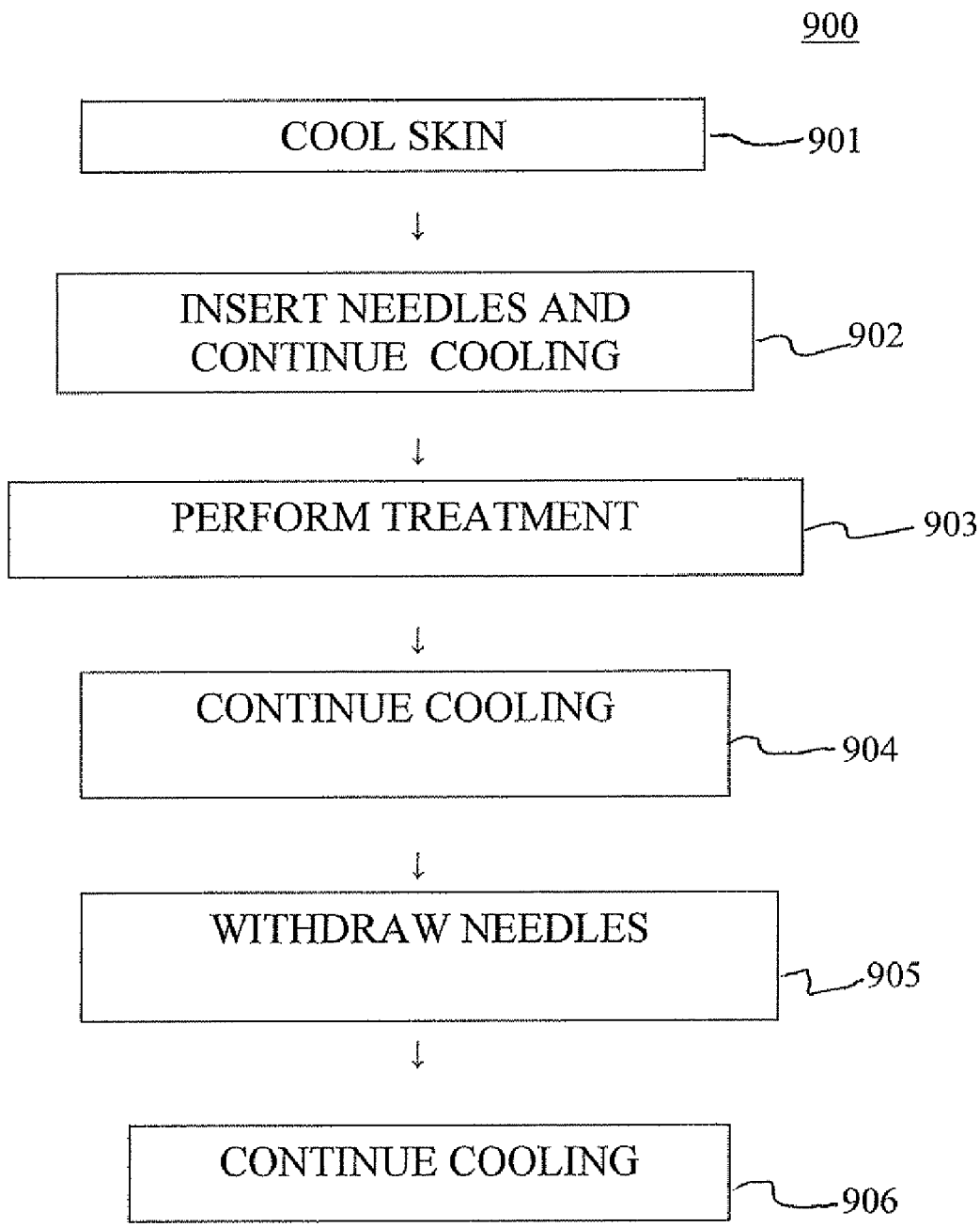
FIG. 9 is a flowchart illustrating typical steps which may be employed to cool the top surface of the skin, prior to, during, and/or after a treatment.

A flowchart 900 in FIG. 9 illustrates methods of cooling the top layer of the skin may be cooled prior to treatment, during treatment, after treatment, or any combination thereof. At step 901, the top surface of the skin is cooled prior to performing the treatment. At step 902, the needles 104-105 of the delivery device 100 are inserted into the skin, and the cooling of the surface of the skin continues. At step 903, the treatment is performed, and at step 904, the cooling of the top surface of the skin continues. At step 905, the needles are withdrawn from the skin and at step 906, the cooling of the top surface of the skin continues. While this example contemplates cooling of the top surface of the skin prior to, during and after treatment, it will be appreciated that cooling may be separately employed in any of the above steps, or in any combination of the above steps. Examples of methods of cooling the top layer of the skin are contact with ice, contact with a cold plate, and/or spraying with a cold fluid or cryogen. Similarly, if desired, the needles may also be cooled. This will assist in preventing any undesirable heating of the top layer of the skin and any resulting untoward effects. This may also reduce any discomfort during treatment.

In accordance with yet another aspect of the subject matter disclosed herein, an energy delivery device 600 may be provided with a retractable needle support 610 or 620, as illustrated by the embodiments shown in FIGS. 6A, 6B and 6C. In accordance with this aspect of the subject matter disclosed herein, delivery device 600 and needles 104-105 are provided with a retractable needle support 610 which surrounds the needles 104-105 and which extends out of the bottom surface 612 of the delivery device 600 as shown in FIG. 6B. Upon insertion of the needles 104-105 into the skin of a patient, the retractable support 610 comes into contact with the skin of the patient and the retractable support 610 is pushed back into the interior of the delivery device 600 as shown in FIG. 6A, thereby permitting the ends of the needles to penetrate the skin for the electric pulse treatment of the tissue. The retractable support 610 thus holds the needles 104-105 in position during insertion and assists in preventing bending of the needles during insertion.

A desirable characteristic of the retractable support 610 is to house the needles 104-105 in a manner which protects the needles from bending or from encountering other damage when not in use. For example, the retractable support 610 may be a tube-like structure of a length sufficient to cover the ends of the needles 104-105, with internal diameters sufficiently large to accommodate the smaller diameter needles, but also of sufficiently small diameter to prevent any significant bending of the needles 104-105 during insertion. Retractable support 610 may be of any suitable shape, such as of a modified oval cross-sectional shape shown in FIGS. 6A and 6B, cylindrical cross-sectional shape, square, rectangular, or other cross-sectional shapes.

Alternatively, a separate retractable support 620 in FIG. 6C may be used about each needle 104 or 105. Retractable support 602 may be of any suitable shape, such as the cylindrical cross-sectional shape illustrated in FIG. 6C. In a manner similar to retractable support 610, each of retractable supports 620 may be pushed back into the interior of the delivery device 600 as the retractable supports come into contact with the skin, thereby permitting the ends of the needles to penetrate the skin for the electric pulse treatment of the tissue.

Either of the retractable supports 610 or 620 may be biased by light pressure supplied, such as by a spring 622 shown in FIG. 6C to extend the supports about the ends of the needles 104-105 when not in use, to retract into the delivery device 600 when in use, and to again extend about the ends of the needles when the treatment is completed. Such a retractable support will also protect the needles from bending or other damage when not in use and may also protect the physician or staff from injury when not in use.

In accordance with another aspect of the subject matter disclosed herein, the delivery device 100 may utilize vacuum-assisted skin engagement. Current and prior art procedures require the physician to hold a delivery device perpendicular to the skin with moderate pressure. If the orientation of the delivery device changes, or if the pressure of the delivery device 100 against the surface of the skin changes, the electrical conditions between the adipose tissue, the pulse generator 300 and the two needles 104-105 may change, resulting in a higher than desired current level. Additionally, air may become entrapped between the needles which may provide a leakage current path.

Illustrated in FIGS. 7A and 7B is a delivery device 700, which may use a light vacuum to assist in pulling the surface of the skin into contact with the bottom surface 704 of the delivery device. Further, once the bottom surface 704 of the delivery device 700 is in engagement with the skin of the patient, the light vacuum assists in retaining the bottom surface of the delivery device in contact with the skin. Thus, any effects due to movement of the patient or the physician are minimized as the patient's skin tends to move with any corresponding movement of the delivery device. For example, the vacuum may be supplied via an orifice 702 in the distal or bottom face 704, such as between needles 104 and 105. Orifice 702 is in the reusable module portion 712 of device 700 which is also in vacuum communication with an internal vacuum passageway 708 in the disposable module portion 710 of device 700. As shown in FIG. 7B, the portion of orifice 702 which meets the bottom surface 704 of the disposable module 710 may be enlarged for application of the vacuum thereat to a correspondingly larger area of the skin. A goal of using a vacuum is to ensure good contact of the delivery device 100 with the skin.

Another embodiment of a disposable needle assembly 720 is shown in FIG. 7B for use with energy delivery device 700. Needles 104-105 electrically connect to delivery device 700, such as by a mini banana plug interface 722, to receive high voltage pulses which are provided by one of the electrical lines 714 or 716 (FIG. 7A) connected to the back end 715 of device 700. The other line 716 or 714 may be used for control signals. Needle assembly 720 includes an outer sleeve 724. The upper end 725 of outer sleeve 724 fits partially into an annular recess 726 defined in the front end 712 of device 700. A ring 728 and 729 of closed cell foam is internally disposed about each needle 104 and 105, respectively. These foam rings 728-729 tend to bias the outer sleeve 724 to the position shown in FIG. 7B where the needles 104-105 are not exposed, but are substantially within outer sleeve 724.

However, when the bottom face 704 of the outer sleeve 724 is applied against the skin of a patient, the foam rings 728-729 are compressed such that needles 104-105 penetrate the skin. At the same time, the upper end 725 of outer sleeve 724 moves upwardly within the annular recess 726. If desired, the limit of needle penetration in the skin can be provided when the upper end 725 contacts the end of the annular groove 726, or when the foam rings 728-729 are fully compressed. The foam rings may be of a foam material which has memory to return to its uncompressed state when a treatment is completed. For example, foam rings 728-729 may be made of a closed cell foam material.

Another embodiment for protecting for the needles 104-105 is shown in FIGS. 8A and 8B. In this embodiment, a sleeve 810 may be retracted for treatment of a patient and the sleeve 810 may be extended when the delivery device 800 is not in use. For example, sleeve 810 may be biased to the extended position shown in FIG. 5B by a spring or the like, in a similar manner to spring 622 in FIG. 6C. Sleeve 810 may be cylindrical in cross-section shape, or oval or other shapes. When sleeve 810 is fully extended, as shown in FIG. 8B, a front edge 814 of sleeve 810 extends forwardly of the tips of needles 104-105. The embodiment shown in FIGS. 8A-8B has some advantages when delivery device uses vacuum assisted treatment. For example, when delivery device 800 is provided with a vacuum orifice, such as orifice 702 shown in FIG. 7B, the entire area within sleeve 810 will be under vacuum as soon as the front edge 814 of sleeve 810 comes into contact with the skin. This will assist in pulling the skin into contact with the needles 104-105 and will also help prevent lateral movement of the delivery device 800 thereby preventing bending of needles 104-105 during insertion.

While particular embodiments of the subject matter disclosed herein have been shown and described, it will be obvious to those skilled in the art that changes and modifications may be made therein without departing from the invention in its broader aspects.

The invention claimed is:

1. A system for providing electrical energy to human tissue to treat a tissue condition, said system comprising:
   a high voltage pulse generator for generating a short high voltage pulse of energy at a pair of output terminals;
   said pulse generator including a spark gap which contains a pressurized gas and which emits a spark when the voltage across the spark gap exceeds the dielectric strength of the gas in the spark gap;
   a sensor for sensing the pressure of the gas in the spark gap and for providing a pressure signal related to the sensed pressure;
   means responsive to the pressure signal for adjusting the pressure in the spark gap to modify the magnitude of the voltage of the short high voltage pulse generated by the pulse generator;
   a delivery device for receiving the short high voltage pulse of energy from the pulse generator and for applying the short high voltage pulse of energy to said tissue; and
   at least a pair of needle electrodes disposed in said delivery device for penetrating into the human tissue and for delivering the short high voltage pulse of energy to tissue disposed between the needle electrodes;
   said spark gap, said sensor and said means for adjusting the pressure in the spark gap all being disposed exterior to said pair of needle electrodes.

2. The system in accordance with claim 1, wherein said needle electrodes of the delivery device have uncoated ends and have an insulative coating applied about proximal portions of the needle electrodes.

3. The system in accordance with claim 1, wherein the delivery device includes more than two needle electrodes such that different pairs of needle electrodes may be selected for delivery of the short high voltage pulse of energy to tissue between the selected pair of needle electrodes.

4. The system in accordance with claim 1, wherein said short high voltage pulse is about 10 nanoseconds to 500 nanoseconds in duration.

5. The system in accordance with claim 1, wherein said short high voltage pulse provides an electric field strength of about 10 kilovolts/centimeter to 50 kilovolts/centimeter in the tissue.

6. The system in accordance with claim 1, wherein a vacuum in the delivery device assists in keeping a bottom face of the delivery device in contact with the human tissue during the treatment.

7. The system in accordance with claim 1,
   wherein the ends of the needle electrodes are retracted into the delivery device and the ends of the needle electrodes are quickly forced into the human tissue upon actuation of the delivery device.

8. The system in accordance with claim 1, further comprising:
   a retractable needle support to protect the needle electrodes from bending during insertion of the needle electrodes into the human tissue.

9. The system in accordance with claim 8, said retractable needle support extending about the ends of the needle electrodes, and said retractable needle support retracting into the delivery device as the needle electrodes are inserted into the human tissue.

10. A system for providing electrical energy to human tissue to treat a tissue condition, said system comprising:
- a high voltage pulse generator for generating a short high voltage pulse of energy at a pair of output terminals;
- said pulse generator including a spark gap which contains a pressurized gas and which emits a spark when the voltage across the spark gap exceeds the dielectric strength of the gas in the spark gap;
- a sensor for sensing the pressure of the gas in the spark gap and for providing a pressure signal related to the sensed pressure;
- means responsive to the pressure signal for adjusting the pressure in the spark gap to modify the magnitude of the voltage of the short high voltage pulse generated by the pulse generator;
- a delivery device for receiving the short high voltage pulse of energy from the pulse generator and for applying the short high voltage pulse of energy to said tissue;
- a controllable gas pressure regulator to supply gas pressure to the spark gap;
- means for selecting an initial voltage magnitude for the short high voltage pulse;
- means for determining the actual voltage magnitude of the short high voltage pulse and for providing a signal representative of the actual voltage magnitude of the short high voltage pulse; and
- a data processor for receiving the signal representative of the voltage magnitude of the short high voltage pulse, said data processor determining any difference between the selected voltage magnitude and the actual voltage magnitude of the short high voltage pulse; and said data processor supplying a corrective signal to the controllable gas pressure regulator to change the gas pressure in the spark gap to decrease the voltage magnitude of the short high voltage pulse if the actual voltage magnitude is greater than the selected voltage magnitude or to increase the voltage magnitude of the short high voltage pulse if the actual voltage magnitude is less than the selected voltage magnitude.

\* \* \* \* \*